(12) United States Patent
Wagner

(10) Patent No.: US 8,138,475 B2
(45) Date of Patent: Mar. 20, 2012

(54) SYSTEM FOR PRODUCING ENHANCED THERMAL IMAGES

(75) Inventor: Matthias Wagner, Cambridge, MA (US)

(73) Assignee: Redshift Systems Corporation, Burlington, MA (US)

( * ) Notice: Subject to any disclaimer, the term of this patent is extended or adjusted under 35 U.S.C. 154(b) by 0 days.

(21) Appl. No.: 13/169,802

(22) Filed: Jun. 27, 2011

(65) Prior Publication Data

US 2011/0254952 A1 Oct. 20, 2011

Related U.S. Application Data

(62) Division of application No. 12/535,084, filed on Aug. 4, 2009, now Pat. No. 7,968,845.

(60) Provisional application No. 61/085,918, filed on Aug. 4, 2008.

(51) Int. Cl.
*G02F 1/00* (2006.01)
(52) U.S. Cl. ........................................................ 250/332
(58) Field of Classification Search .................. 250/330, 250/332, 334, 338.4, 339.01, 339.04; 348/135, 348/E7.085
See application file for complete search history.

(56) References Cited

U.S. PATENT DOCUMENTS

| | | | | |
|---|---|---|---|---|
| 3,791,097 A | * | 2/1974 | Cassella et al. | 52/745.06 |
| 4,494,881 A | * | 1/1985 | Everest | 374/124 |
| 5,959,589 A | * | 9/1999 | Sadovnik et al. | 343/765 |
| 6,281,970 B1 | * | 8/2001 | Williams et al. | 356/141.4 |
| 7,220,966 B2 | * | 5/2007 | Saito et al. | 250/341.6 |
| 7,561,181 B2 | * | 7/2009 | Schofield et al. | 348/148 |
| 2004/0183904 A1 | * | 9/2004 | Johnson | 348/144 |

* cited by examiner

*Primary Examiner* — David Porta
*Assistant Examiner* — Marcus Taningco
(74) *Attorney, Agent, or Firm* — BainwoodHuang

(57) ABSTRACT

An imaging device has a thermal sensor to remotely measure respective temperatures of regions within an imaging field and to generate temperature information signals. A motion tracking system tracks motion of the thermal sensor and generates position information signals representing positions of the thermal sensor during the temperature measurements. An image construction processor uses the position and temperature information signals to generate a two-dimensional image representative of the imaging field including respective temperature indications at different locations within the two-dimensional image, and stores the two-dimensional image within a memory. The two-dimensional image may be used as an output image for display to a user.

14 Claims, 4 Drawing Sheets

SYSTEM FOR PRODUCING ENHANCED THERMAL IMAGES

BACKGROUND

Thermal cameras are used for a variety of building inspection applications including insulation, moisture, electrical faults, HVAC and even stud-finding in walls. In addition there are myriad applications in industrial or utility settings where thermal images are desirable for preventative maintenance operations.

The high cost of high-resolution thermal imaging has severely constrained the size of the market for thermal inspection cameras. In many cases users settle for single-point "spot" infrared thermometers and gather only a fraction of the thermal information, often at the expense of significant time and effort where multi-point measurements are needed. There has been a choice between single-point measurements and complete two-dimensional images, with pricing of the devices for the two approaches being one to two orders of magnitude apart.

SUMMARY

The present invention discloses a method of using low-cost single-point infrared sensors or low-resolution infrared sensor arrays to generate a higher-resolution thermal image of the inspection subject.

In one aspect, an imaging device is disclosed which includes a thermal sensor configured with optics to remotely measure respective temperatures of a plurality of regions within a scene and to generate corresponding temperature information signals. A motion tracking system tracks motion of the thermal sensor and generates relative position information signals representing the plurality of positions of the thermal sensor during the temperature measurement of the plurality of regions. An image construction processor uses the relative position information signals to map the locations of the plurality of regions to a corresponding plurality of locations within an image representative of the imaging field. The image construction processor also uses the temperature information signals to map the measured temperatures of the plurality of regions to corresponding temperature indications for the plurality of locations respectively within the image, and stores the image within a memory. The two-dimensional image may be used as an output image for display to a user.

In another aspect an imaging device includes a first sensor operative to receive first sensor input in a first wavelength band from a first sensor imaging field and to generate a corresponding first sensor output signal, and a second sensor operative to receive second sensor input in a second wavelength band from a second sensor imaging field and to generate a corresponding second sensor output signal. The second sensor imaging field contains and is larger in extent than the first sensor imaging field, and the first and second sensor imaging fields are of known spatial and temporal registration with respect to each other. The imaging device further includes image processing circuitry which receives the first and second sensor output signals in a first time slot when a first scene of interest is viewed, and receives the first and second sensor output signals in a second time slot when a second scene of interest is viewed. The second sensor imaging field in the first time slot has an overlapping spatial region with the second sensor imaging field in the second time slot. The image processing circuitry also analyzes the second sensor output signals from the first and second time slots to detect motion and to map the first sensor output signals into a two-dimensional image representative of regions within the first and second scenes of interest, and stores the two-dimensional image within a memory.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

DETAILED DESCRIPTION

Figure 1:
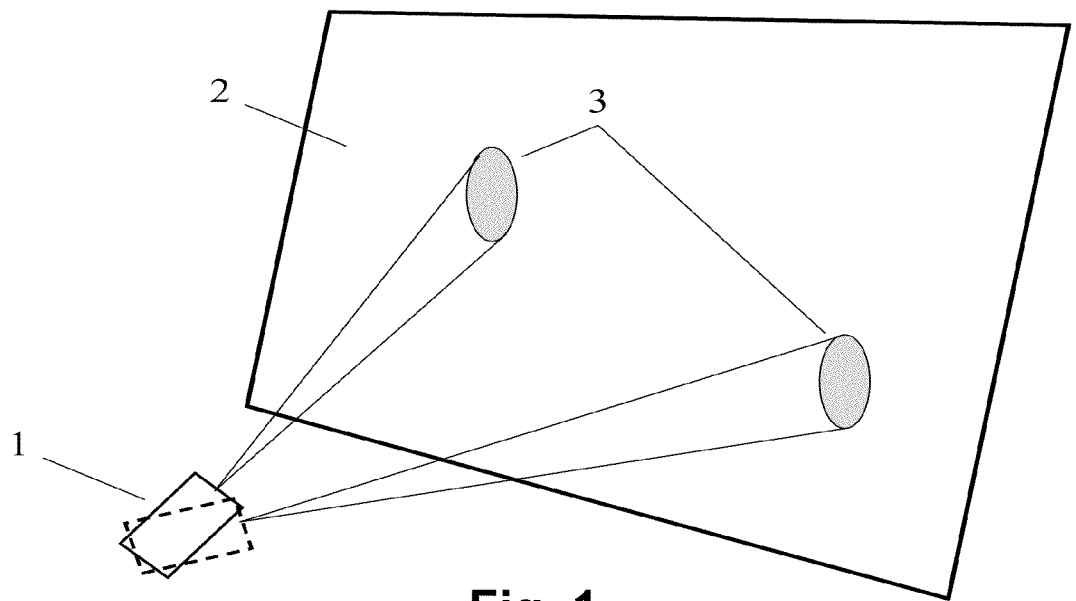
FIG. 1 is a diagram illustrating use of a spot infrared sensor to temperature data at multiple points of an object of interest.

FIG. 1 illustrates the use of a standard spot infrared thermometer or thermal infrared sensor for inspection of a scene. The infrared sensor 1 is pointed at a scene of interest 2, and a temperature data point is recorded for a measurement area 3, which is defined by the pointing direction of the infrared sensor 1, the distance from the infrared sensor 1 to the scene 2, and the field of view of the infrared sensor 1. Multiple data points may be taken across the scene of interest 2, each at a different time (or equivalently each in a different time slot) to identify temperature gradients or differentials that vary spatially and/or temporally across the scene of interest 2. These data points, read out as absolute or relative temperatures, may be observed by a user directly (perhaps for an immediate assessment or decision about the scene of interest 2), or they may be logged as a series, either on a separate piece of paper or device, or internally in the case of more sophisticated versions of the infrared sensor 1.

Figure 2:
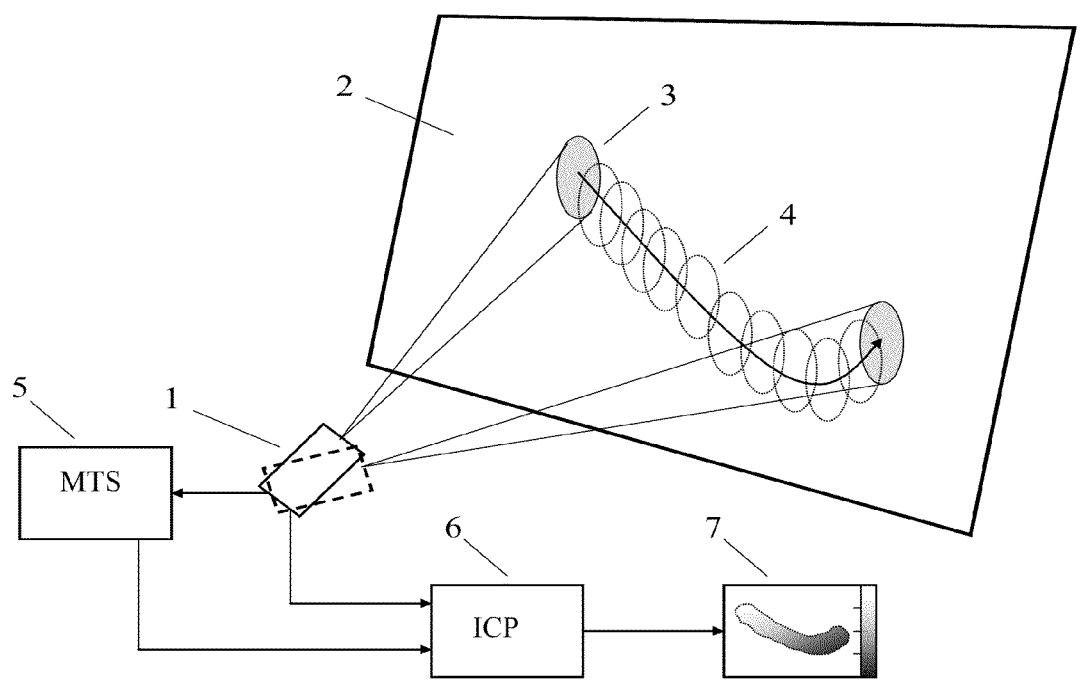
FIGS. 2-7 are block diagrams of different systems using an infrared sensor along with motion tracking and image construction to generate a two-dimensional thermal image of an object of interest.

FIG. 2 shows a system in which the infrared sensor 1 is scanned over the scene of interest 2 along a trajectory 4 while sampling a plurality of measurement areas 3 each in their respective time slot. The trajectory 4 may be established by some mechanical means or by a user's hand in the case of a handheld device. The trajectory 4 may be along a one dimensional track, a two dimensional raster, or may be any other motion of some spatial extent and time duration. The infrared sensor 1 may also be used to indicate trajectory to a user based on, by way of example, a predetermined track relative to an initial starting position, or by indicating a future trajectory based on past trajectory. In this manner, the sensor 1 can help ensure that the desired spatial range of temperature measurements across the scene is achieved. This is particularly advantageous for a hand held thermal sensor. Indication of trajectory to the user may be by visual means, as provided for in a display, by audible means, such as with a pitched tone, or by tactile means, such as provided for in a vibrator or internal gyroscope.

Returning to a description of FIG. 2, in parallel with the temperature measurement samples provided by the infrared sensor 1, a motion tracking subsystem (MTS) 5 tracks the relative motion of the infrared sensor 1 while sampling each of the plurality of measurement areas 3 along the trajectory 4. An image construction processor (ICP) 6 accepts the plurality of temperature readings from the infrared sensor 1 along with corresponding position estimates from the MTS 5 and constructs a corresponding a thermal image which represents the distribution of measured temperature across the scene of interest 2, as if the user were "painting" temperature information onto the thermal image. The thermal image may be one or two dimensional, depending on the number of samples and the trajectory 4. The constructed image may represent temperature data using a color or grayscale mapping, for example. The image may be stored in a memory for later use, and/or displayed on a graphical output device 7 which may be a display screen on the infrared sensor 1 for example.

Alternatively, the computed thermal image may be superimposed onto the scene of interest 2 by an optical image projector system (not shown in FIG. 2).

Mechanical Motion Tracking

Figure 3:
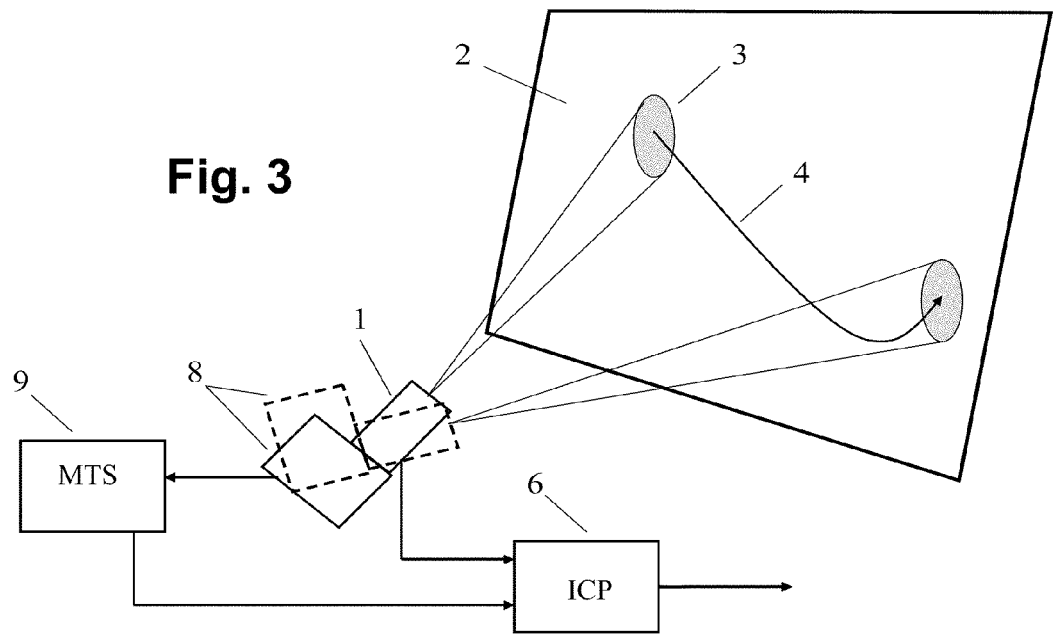

FIG. 3 shows one of several possible methods by which motion tracking may be implemented to produce data to estimate the trajectory of the infrared sensor 1. The system of FIG. 3 may employ mechanical sensors in the measurement unit itself. As the infrared sensor 1 is scanned over the scene of interest 2, one or more sensors making up a mechanical tracking unit 8 gather relative data on angle and/or position. This data is processed by the motion tracking subsystem 9 to calculate position relative to a starting point, and the position information is utilized as described above.

The mechanical tracking unit 8 may consist of a number of types of sensors including but not limited to magnetic angle sensors (generally to give angle relative to the earth's magnetic pole), accelerometers for measuring tilt using gravity (assuming very slow acceleration from sweeping motion) or other means, gyros for measuring angle changes, and various combinations of sensors providing different levels of accuracy. Many of these sensors are becoming compact and cost-effective due to integration into micro-electromechanical systems. Optionally a range finder, such as a laser range finder, may be added to the system in order to track motion of the measurement point in three dimensions and motion relative to the scene. Such a range finder may be used for other purposes in the instrument such as making adjustments for atmospheric effects in the infrared.

Video Motion Tracking

Image sensors offer another method of motion tracking during acquisition of infrared temperature data. Image sensor components and associated electronics have become very cost-effective, and image-based motion estimation algorithms have been optimized for low power due to the need to provide accurate motion estimates in video compression algorithms. Multiple low-cost microprocessors have specialized hardware for the purpose of performing real-time motion estimates.

Figure 4:
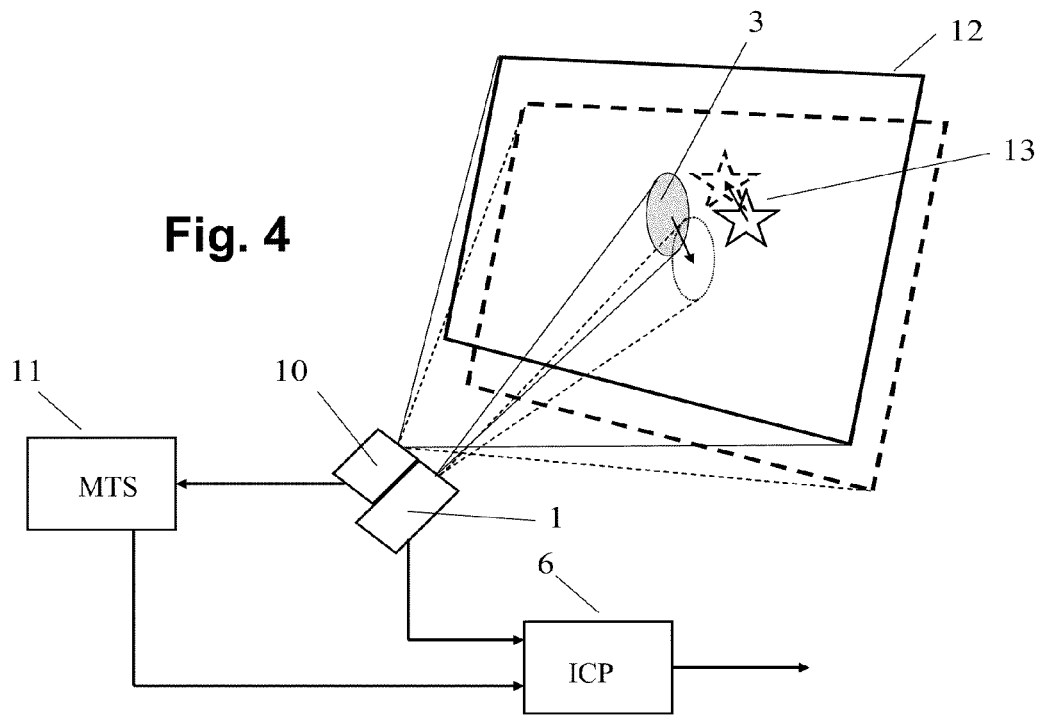

FIG. 4 shows an example of a system employing a video-based motion tracking system. In this embodiment, the infrared sensor 1 is combined with a video image sensor 10 which observes a video imaging field 12 around the temperature measurement area 3. The infrared sensor 1 and video image sensor 10 are of known spatial registration with respect to each other. They may also be of known temporal registration with respect to the timing of the measurements being performed by each sensor. The timing of the two sensors may be coincident, overlapping, or at different times. Typically the video image sensor 10 will operate in the visible or near infrared region of the spectrum, for which there are low-cost image sensors widely available. Within the video imaging field 12 there are one or more visible objects 13. As the video image sensor 10 is swept along a trajectory 4 as described previously, the position of the visible object 13 within the video imaging field 12 moves opposite to the direction of motion of the video image sensor 10. The motion tracking subsystem 11 compares successive overlapping video frames from the video image sensor, 10 each taken in a different time slot, using well-known video motion estimation techniques in order to calculate motion from one frame to the next. The techniques may be optimized for this application in order to provide the most accurate possible estimates for image motion in the portion of the field where the temperature sensing area 3 is located. The apparent motion of the objects 13 in the image is inverted in order to calculate the trajectory of motion of the temperature sensing area 3 over the scene. The information may then be used to construct a thermal image as described previously.

Optionally, the video image sensor 10 may be used for a number of additional functions in the instrument. It may of course be used to obtain a visible image of the scene of interest in the vicinity of the temperature measurement area 3 in order to provide a user reference for the temperature measurements. A series of temperature measurements along a trajectory may then be superimposed or blended with this visible image to create a composite or "fusion" image. As the area of measurement 3 moves, and the video imaging field 12 moves accordingly, it may be desirable to overlay and "stitch" successive imaging field 12 images from the video image sensor 10 in order to form an image with an effectively wider or narrower field of view than the image field 12, corresponding to the region of interest for the temperature measurements.

Video Motion Tracking with Active Light Source

In certain applications the object of interest may be devoid of visible features for tracking, or ambient lighting conditions may prevent the use of a visible imager. In this case it may be desirable to actively provide lighting onto the object of interest, preferably structured in a way to provide maximum contrast on the object of interest and facilitate tracking.

Figure 5:
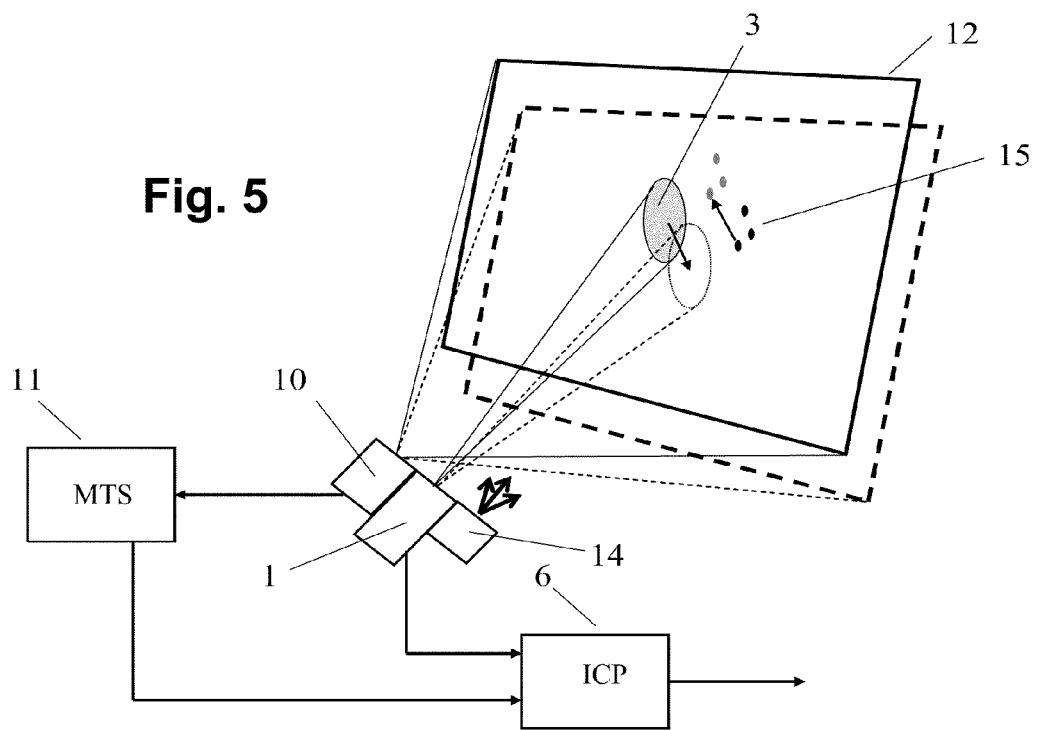

FIG. 5 shows an embodiment incorporating a lighting system for such active lighting. A laser source 14 such as a laser diode is incorporated with the infrared sensor 1 such that its beam is approximately collinear with the sensing axis of the infrared sensor 1. The laser source 14 projects light within and possibly surrounding the measurement area 3. Because light from the laser source 14 is coherent, it produces a speckle interference pattern 15 on the surface of the object. This speckle pattern is particular to the local object surface texture. As a result, as the infrared sensor 1 is moved and the measurement area 3 is translated over the object surface, there is a corresponding but opposite shift in the characteristic speckle pattern. This shifting of the speckle pattern allows accurate image-based motion estimation using the image sensor 10 and image motion tracking subsystem 11 even when few or no obvious features exist on the object. Optionally, the infrared sensor 1 and motion tracking subsystem 11 are integrated into a single component, such as found in laser-based optical computer mice for example which operate on the same principle for tracking motion over a surface.

Extension to Multi-Pixel Temperature Sensor

The disclosed technique may be applied equally well to a multi-pixel infrared temperature sensor for the purpose, identically, of creating an output thermal image with more spatial resolution than the infrared sensor has pixels.

Figure 6:
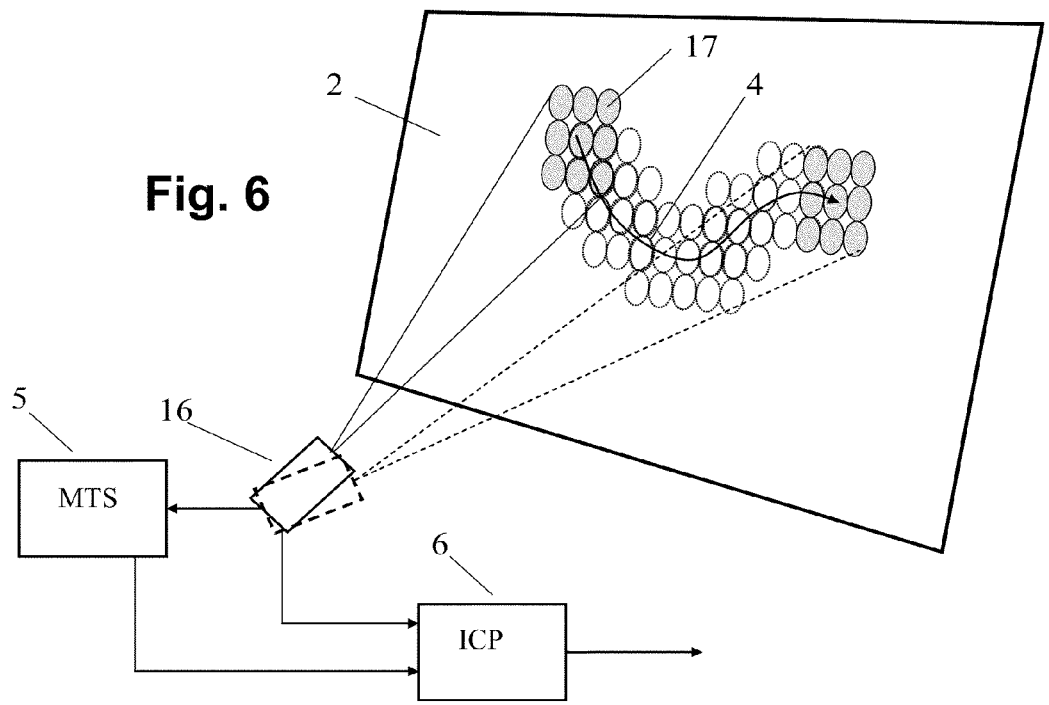

FIG. 6 shows one such system. In this example, an infrared sensor 16 containing imaging optics and an array of sensing pixels measures the temperature of an array of measurement areas 17 (or equivalently an instantaneous infrared imaging field of multiple pixels) in a scene of interest 2 and in a first time slot. In this case the measurement areas 17 sample an area that is small relative to the desired total measurement area. The infrared sensor 16 may be scanned along a measurement trajectory 4, and the array of measurement areas 17 data each taken in a different time slot may be used in place of the scalar temperature data in any of the above-described systems/methods. That is, the trajectory is tracked by an MTS 5 and the position information is fed along with the temperature measurement information to the image construction processor 6 which assembles the individual images into a complete "mosaic" to provide an effectively wider field of view composite temperature image than of the array of measurement areas 17 alone.

Figure 7:
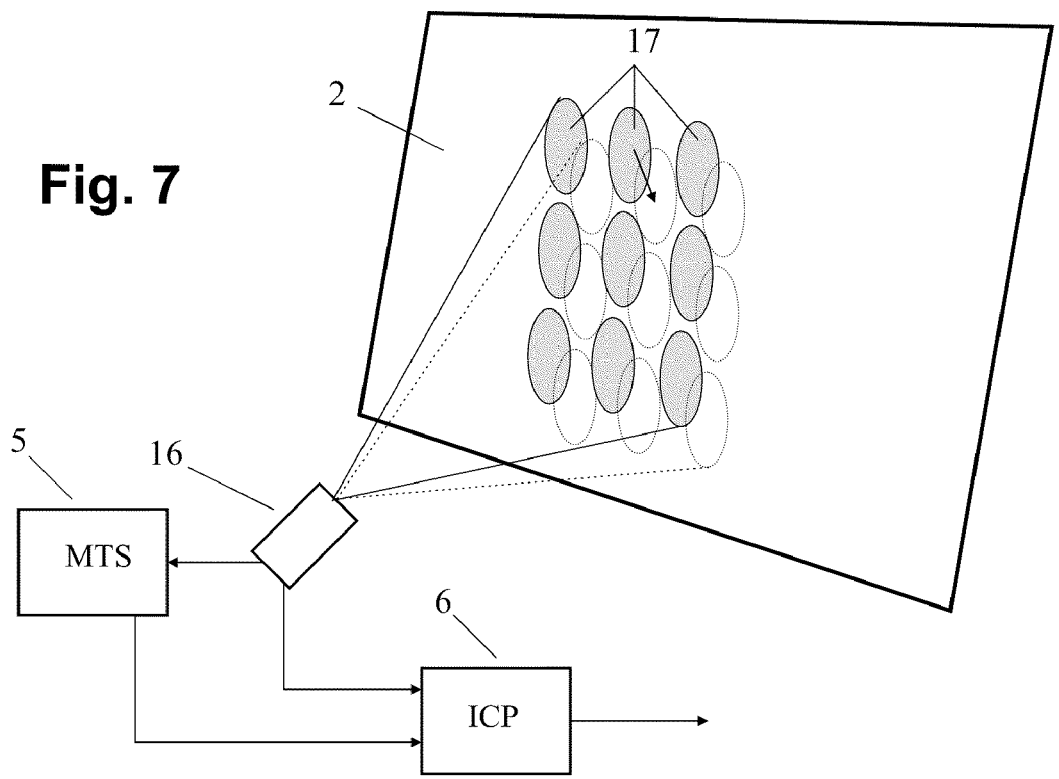

FIG. 7 shows another embodiment in which motion tracking is used to enhance effective spatial resolution within the field of view of the temperature sensors array. An infrared sensor 16 with an array of sensing pixels measures temperature in an array of measurement areas 17 in a scene of interest 2. In order to enhance the effective spatial resolution within the measurement area, sub-pixel motion is tracked using one of the methods described above (this motion may be the result of inadvertent hand motion in a portable device). The tracked motion is reported by the motion tracking subsystem 5 to the image construction processor 6 which assembles the individual readings together with position estimates and via well-known image processing algorithms reconstructs a higher-resolution image. This method may in fact be combined with the mosaic-generating method described above to provide an image with both effectively higher spatial resolution and larger field of view than the infrared sensor 16 can itself provide.

As mentioned, the motion of the infrared sensor 1 can be provided by a user, as in the case in a handheld instrument, but it may of course be provided mechanically using one of a number of systems for creating motion. For example, a motor can be used to turn the infrared sensor 1 around the top of a tripod in order to create a mosaic, 360-degree view of a room, and a motion tracking system provides accuracy in reconstructing the complete scene. At the same time, this motion can provide the ability to do pixel super-resolution along the horizontal axis. Similarly, mechanical means may be used to dither the pointing angle of the infrared sensor 1 slightly along either/both horizontal and vertical axes to provide a super-resolved image using the means described above.

The duration of the time slots as well as the time duration between respective time slots may be selected based on the attributes of the sensors used, the range and speed of motion, and the requirements of the application. For example, rapid motions of the sensor typically require shorter duration time slots and a shorter interval between time slots to achieve the desired spatial resolution. The interval between time slots may also be selected based on the dynamics of the scene. For example, to capture scenes containing rapidly varying temperatures (i.e. higher frequency), the time interval between time slots must be adjusted downward to measure the temperature changes. The interval between time slots may be predetermined or user selected, such as by the user pressing a button to capture a temperature reading. The interval may also be based on measurements of motion in an active feedback method. For example, as faster motion is sensed, the time interval may be shortened in order to maintain a certain level of spatial resolution. Feedback may also be provided to the user, for example by an audible tone, to indicate a desired rate of movement for a particular time interval capability of the sensor, as for example in a handheld application.

Additional Thermal Signal Enhancement

In the present invention, when multiple thermal readings are taken from the same apparent location, they may be averaged in order to reduce the level of noise in the temperature reading, and increase the accuracy of the calculated output. In the case of a multi-pixel thermal infrared sensor, multiple readings of overlapping scene locations from a diversity of thermal sensor pixels may be used to (a) "fill in" thermal information in the case of a bad sensor pixel; or (b) calculate differences in thermal pixel responses in real time, and compensate for these in the reproduced thermal image and thereby provide a more uniform image; or (c) average different pixel signals when viewing the same spatial location in the scene of interest to improve signal to noise ratio.

Thermal Pixel Arrangement and Orientation

In the case of thermal infrared sensors having multiple pixels, it may be desirable to orient the infrared sensor in a particular manner relative to the predominant motion direction and desired information. For instance, if a linear array of thermal sensors is used, orientation perpendicular to the axis of motion is faster to "fill in" a complete thermal image of the scene; while orientation parallel to the axis of motion generates very accurate thermal readings through pixel averaging in a manner known to those skilled in the art as time delay and integration.

Other Wavelengths

The disclosed technique may be useful in applications where current high-resolution sensors are used. Because only a single sensor element or sensor with a small number of elements is used, the technique may provide a cost advantage while still providing a user with a desired a higher-resolution image. Thermal imaging is an example of such an "expensive" wavelength range for imaging, but the technique may be applied to other wavelengths using similar means for tracking motion and constructing higher-resolution images. Examples of wavelengths where this may be desirable include but are not limited to millimeter-wave and terahertz radiation.

While various embodiments of the invention have been particularly shown and described, it will be understood by those skilled in the art that various changes in form and details may be made therein without departing from the spirit and scope of the invention as defined by the appended claims.

What is claimed is:

1. An imaging device, comprising:
    a first sensor operative to receive first sensor input in a first wavelength band from a first sensor imaging field and to generate a corresponding first sensor output signal;
    a second sensor operative to receive second sensor input in a second wavelength band from a second sensor imaging field and to generate a corresponding second sensor output signal, the second sensor imaging field containing and being larger in extent than the first sensor imaging field, the first and second sensor imaging fields being of known spatial and temporal registration with respect to each other; and
    image processing circuitry operative to:
        (1) receive the first and second sensor output signals in a first time slot when a first scene of interest is viewed,
        (2) receive the first and second sensor output signals in a second time slot when a second scene of interest is viewed, wherein the second sensor imaging field in the first time slot has an overlapping region with the second sensor imaging field in the second time slot; and
        (3) analyze the second sensor output signals from the first and second time slots to detect motion and to map the first sensor output signals into a two-dimensional image.

2. The imaging device of claim 1 wherein the first sensor is an infrared point thermometer.

3. The imaging device of claim 1 wherein the first sensor is a two-dimensional thermal imaging sensor.

4. The imaging device of claim 1 within the two dimensional image further comprises information representative of the second sensor imaging field.

5. The imaging device of claim 1 wherein the motion tracking system uses laser speckle as a basis for determining motion.

6. The imaging device of claim 1 wherein the first sensor imaging field in the first time slot overlaps with the first sensor imaging field in the second time slot.

7. The imaging device of claim 6 wherein the regions of overlapping signals are temporally averaged to improve signal to noise ratio in the two dimensional image.

8. The imaging device of claim 6 wherein the regions of overlapping signals are processed to improve spatial resolution in the two dimensional image.

9. The imaging device of claim 6 wherein the regions of overlapping signals are processed to improve image uniformity in the two dimensional image.

10. The imaging device of claim 1 wherein the second sensor imaging field in the first time slot is different from the second sensor imaging field in the second time slot by virtue of human movement of the imaging device.

11. The imaging device of claim 1 wherein the interval between time slots is selected based on the rate of change of time varying thermal signals.

12. The imaging device of claim 1 wherein the interval between time slots is selected based on the detected motion.

13. The imaging device of claim 1 wherein the device provides an indication to the user of the future motion of the device.

14. The imaging device of claim 13 wherein the future motion is based on past motion.

* * * * *